US005626138A

United States Patent [19]
Hossack et al.

[11] Patent Number: 5,626,138
[45] Date of Patent: May 6, 1997

[54] ULTRASONIC TRANSDUCER PROBE WITH AXISYMMETRIC LENS

[75] Inventors: John A. Hossack; John W. Eaton, both of Palo Alto; Thomas G. Cooper, Menlo Park, all of Calif.

[73] Assignee: Acuson Corporation, Mountain View, Calif.

[21] Appl. No.: 482,922

[22] Filed: Jun. 7, 1995

Related U.S. Application Data

[63] Continuation-in-part of Ser. No. 267,318, Jun. 28, 1994, Pat. No. 5,562,096.
[51] Int. Cl.$^6$ ............................................. A61B 8/12
[52] U.S. Cl. ........................... 128/662.06; 128/662.03
[58] Field of Search ........................ 128/660.1, 662.03, 128/662.06, 663.01

[56] References Cited

U.S. PATENT DOCUMENTS

| | | | |
|---|---|---|---|
| 3,387,604 | 6/1968 | Erikson | 128/662.06 |
| 3,546,012 | 12/1970 | Dixon et al. | 128/662.06 |
| 3,958,559 | 5/1976 | Glenn et al. | 128/662.06 |
| 4,001,766 | 1/1977 | Hurwitz | 128/662.06 |
| 4,131,025 | 12/1978 | Mezrich et al. | 128/662.06 |
| 4,184,094 | 1/1980 | Kopel | 128/662.06 |
| 4,205,686 | 6/1980 | Harris et al. | 128/662.06 |
| 4,387,720 | 6/1983 | Miller | 128/662.06 |
| 4,543,960 | 10/1985 | Harui et al. | 128/662.06 |
| 4,567,895 | 2/1986 | Putzke | 128/662.06 |
| 4,572,201 | 2/1986 | Kondo et al. | 128/662.06 |
| 4,762,002 | 8/1988 | Adams | 128/662.06 |
| 4,880,012 | 11/1989 | Sato | 128/662.06 |
| 4,945,915 | 8/1990 | Nagasaki | 128/662.06 |
| 5,078,149 | 1/1992 | Katsumata et al. | 128/662.03 |
| 5,127,410 | 7/1992 | King et al. | 128/662.06 |
| 5,176,142 | 1/1993 | Mason | 128/662.06 |
| 5,207,225 | 5/1993 | Oaks et al. | 128/662.06 |
| 5,226,422 | 7/1993 | McKeighen et al. | 128/662.06 |
| 5,297,553 | 3/1994 | Sliwa, Jr. et al. | 128/662.06 |
| 5,299,578 | 4/1994 | Rotteveel et al. | 128/662.06 |
| 5,305,755 | 4/1994 | Nakao | 128/662.06 |
| 5,320,104 | 6/1994 | Fearnside et al. | 128/662.06 |
| 5,402,793 | 4/1995 | Gruner et al. | 128/662.06 |
| 5,465,724 | 11/1995 | Sliwa et al. | 128/662.03 |
| 5,469,852 | 11/1995 | Nakamura et al. | 128/662.06 |

OTHER PUBLICATIONS

Article Entitled, "Transoesophageal cross–sectional echocardiography with a phased array transducer system Technique and initial clinical results" by M. Schluter, B A Langenstein, J Polster, P Kremer, J Souquet, S Engel and P Hanrath, Accepted for Publication: 1 Apr. 1982.

*Primary Examiner*—Francis Jaworski
*Attorney, Agent, or Firm*—Brinks Hofer Gilson & Lione

[57] ABSTRACT

According to the present invention, an ultrasonic transducer probe is provided having an array of ultrasonic transducers rotatably mounted about an axis within the ultrasonic transducer probe, a lens mounted to the array, and a housing encasing the array and the lens. The lens is symmetric about the axis of rotation of the array. In addition, the housing has a continuous upper surface that is formed, in a region adjacent to the symmetric lens, to mate with the symmetric lens.

18 Claims, 4 Drawing Sheets

ULTRASONIC TRANSDUCER PROBE WITH AXISYMMETRIC LENS

This is a continuation-in-part of application Ser. No. 08/267,318 filed on Jun. 28, 1994, and now U.S. Pat. No. 5,562,096.

BACKGROUND OF THE INVENTION

The invention relates to ultrasonic imaging systems, and more particularly to systems that utilize an acoustic lens to focus ultrasonic energy.

The users of medical ultrasonic transducer probes, hereinafter referred to as sonographers, can obtain images of a region within a body by properly positioning a probe against the body. In order to obtain images having diagnostic value, the sonographer may have to physically manipulate the position of the probe by sliding, rotating, and tilting the probe. One area in particular where this manipulation is more challenging is transesophageal cardiac imaging. During transesophageal cardiac imaging, the sonographer positions a transducer housing at the tip of the probe against the esophagus or stomach of a patient in order to obtain different fields of view of the heart.

Typically for this application, the transducer housing contains a number of acoustic transducer elements, which may be sequentially electrically excited by an ultrasound control and operating system to obtain an image in an object plane that is perpendicular to the transducer housing and the transducer elements. It has been found desirable to rotate the transducer elements contained within the transducer housing independently from the physical manipulation of the housing itself. In combination with the ability to slide, rotate and tilt the transducer housing, the ability to independently rotate the transducer elements within the housing gives the sonographer the ability to obtain an ultrasonic image of any or all object planes orthogonal to the upper surface of the transducer elements at each location to which the housing can be moved.

Because the transducer housing on this type of probe may be placed within the body of the patient being examined, it must be sealed to protect against the ingress of bodily fluids, sterilant solutions, and cleaning solutions. The seal may also prevent moving parts, such as the rotating transducer elements, from contacting the body of the patient.

The acoustic energy radiated from the transducer housing may be focused by mounting an acoustic lens to the transducer elements within the housing. A cylindrical lens, which does not vary in thickness along the azimuthal direction, is sometimes used to provide a fixed focus to the transducer array in the elevation direction.

Devices are known that utilize a cylindrical lens. For example, U.S. Pat. No. 5,127,410 to King et al. includes a compound lens secured on top of a rotatable transducer. The compound lens may have a convex cylindrical lens of a first material mated to a concave lens of a second material. The second material has substantially the same acoustic properties as the body being scanned. The concave portion of the compound lens is shaped so that the upper surface of the compound lens is flat. The flat upper surface of the compound lens is mated to a flat lens assembly that seals an opening in the transducer housing. The opening is sealed, for example by a thin plastic film that is bonded to the housing in the area around the opening. A backing layer is formed to the plastic film and an RFI screen is embedded in the backing layer. A grease layer lubricates the interface between the flat upper surface of the compound lens and the flat lens assembly that seals the transducer housing.

A disadvantage of the King device is that a number of material layers are added to the top of the transducer elements, which can cause degraded performance due to attenuation within the layers or reflections at the material interfaces giving rise to reverberation artifacts in the resultant image. In addition, the concave lens may be difficult to fabricate. Few solid materials possess the acoustic properties required of the concave lens, and those materials that do possess the required properties may not adhere to the convex lens material and may absorb certain grease or oil materials causing the concave lens to expand. Expansion of the concave lens may lead to distortion of the transducer housing's component parts, unreliability, and a reduction in image quality. Furthermore, the added process steps in fabricating and assembling each material layer may decrease yield.

A further disadvantage of the King device is that the compound lens may require more space within the transducer housing than would a simple lens. It is desirable to minimize the size of the transducer housing so that it may be easily inserted by the sonographer and manipulated within the body of the patient without causing excessive patient discomfort.

A further disadvantage of the King device is that the flat lens assembly that seals the opening in the transducer housing may deform or make poor contact with the body of the patient upon application of pressure by the sonographer. It is desirable to maintain acoustic contact with the body of the patient because the presence of any gaps between the transducer housing and the patient will seriously degrade performance.

A still further disadvantage of the King device is that additional process steps are required to seal the opening in the housing and the seal may introduce additional material layers between the transducer elements and the body of the patient. As noted above, it is desirable to minimize the number of material layers between the transducers and the patient and to minimize processing steps in constructing the transducer housing.

Accordingly, it would be desirable to have an improved ultrasonic transducer probe.

SUMMARY OF THE INVENTION

According to a first aspect of the present invention, an ultrasonic transducer probe is provided having an array of ultrasonic transducers mounted within the ultrasonic transducer probe, a lens mounted to the array, and a housing encasing the array and the lens. The housing has a continuous surface adjacent to the lens.

According to a second aspect of the present invention, an ultrasonic transducer probe is provided having an array of ultrasonic transducers rotatably mounted about an axis within the ultrasonic transducer probe, a lens mounted to the array, and a housing encasing the array and the lens. The lens is symmetric about the axis of rotation of the array. In addition, the housing has a continuous upper surface that is formed, in a region adjacent to the symmetric lens, to mate with the symmetric lens.

According to a third aspect of the present invention, an ultrasound system for providing diagnostic information from the interior of a body is provided having an ultrasonic transducer probe, an operating and control system for processing electrical signals produced by the ultrasonic transducer probe, and means for operatively coupling the ultrasonic transducer probe to the operating and control system.

The transducer probe has an array of ultrasonic transducers, an axisymmetric lens mounted to the array, and a housing encasing the array and the lens. The housing has a continuous surface adjacent to the lens.

According to a fourth aspect of the present invention, a method of providing diagnostic information from the interior of a body is provided having the steps of providing an ultrasound system having transmitting electronics, receiving electronics, an array of ultrasonic transducer elements and an axisymmetric lens attached to the array, storing values corresponding to a propagation time through the axisymmetric lens and an angle of refraction at an interface between the lens and the body for a set of acoustic lines, adjusting the transmitting electronics and the receiving electronics in accordance with the stored values, and transmitting acoustic pressure waves into the body and receiving acoustic echoes from the body through the axisymmetric lens on the set of acoustic lines.

DETAILED DESCRIPTION OF THE PRESENTLY PREFERRED EMBODIMENTS

The present invention is best understood by reference to the embodiments shown in FIGS. 1 to 5 where like elements are referred to by like numerals. FIG. 1A shows a transducer housing 2 containing a rotating transducer array 4. A lens 6 is positioned adjacent to the transducer array 4. Preferably, the lens 6 is symmetric about an axis of rotation 8 of the transducer array 4. Lenses having the property of being symmetric about an axis of rotation are referred to herein as axisymmetric lenses. Parabolic lenses, spherical lenses, and hyperbolic lenses are examples of axisymmetric lens.

Figure 1A:
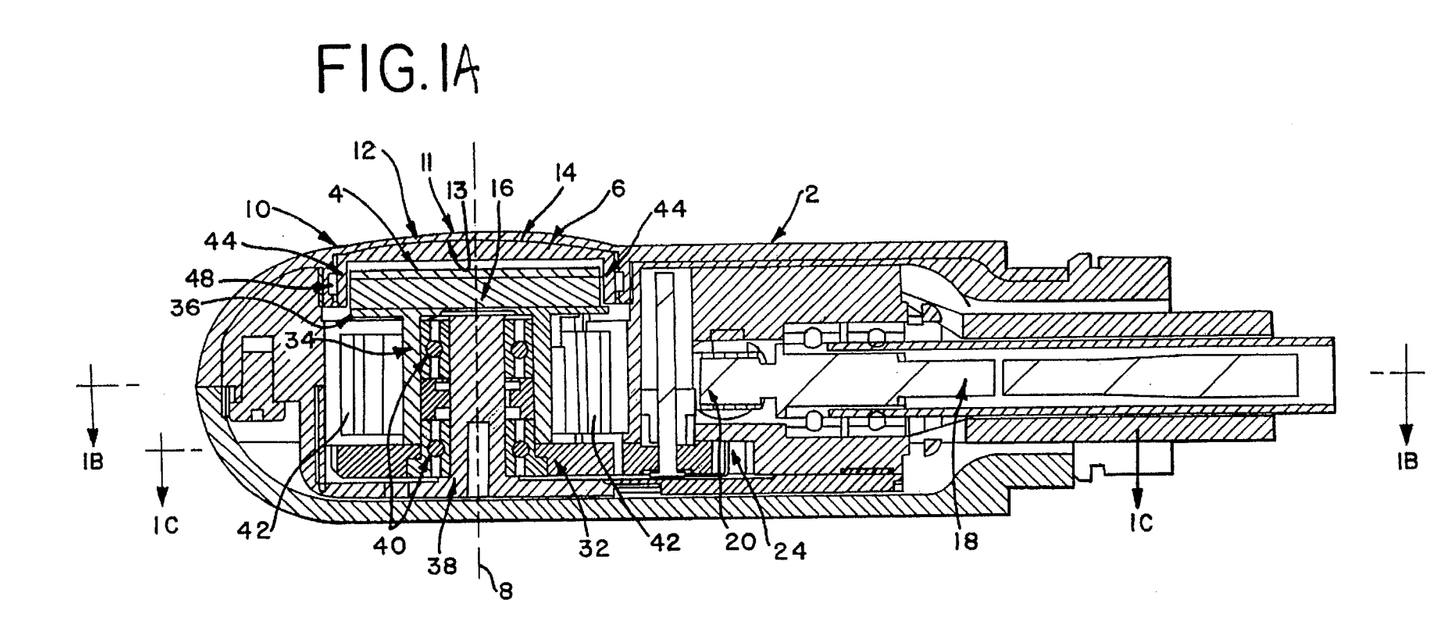
FIGS. 1A through 1C are sectional views of a transducer probe in accordance with the present invention.
Figure 1B:
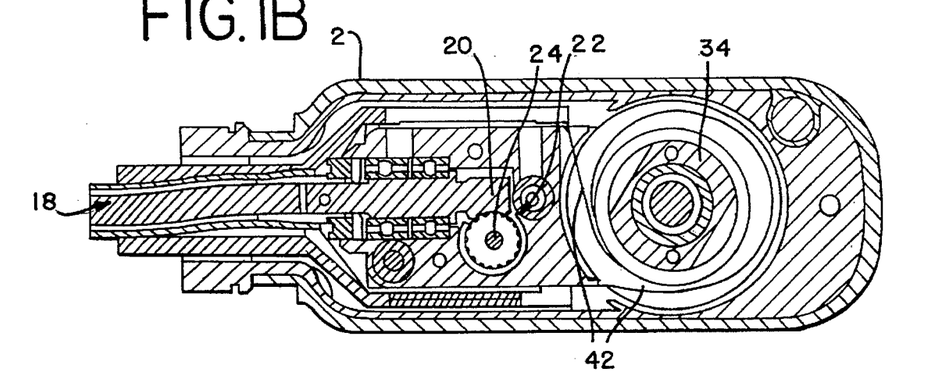
Figure 1C:
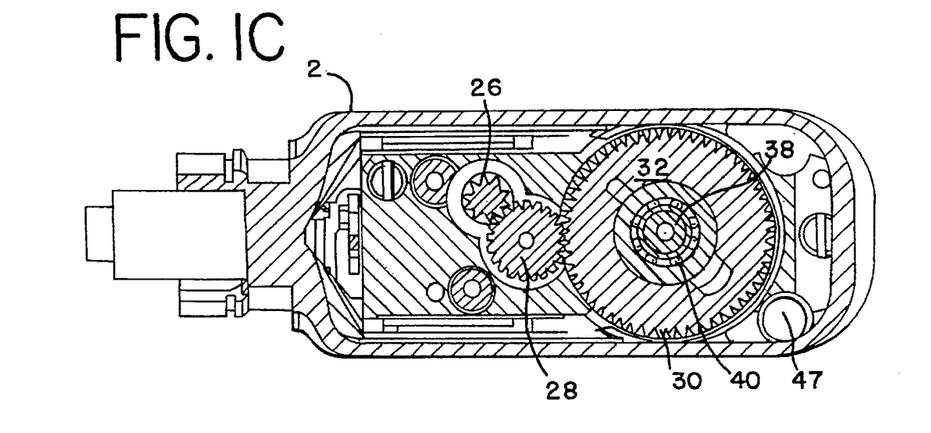
Figure 2:
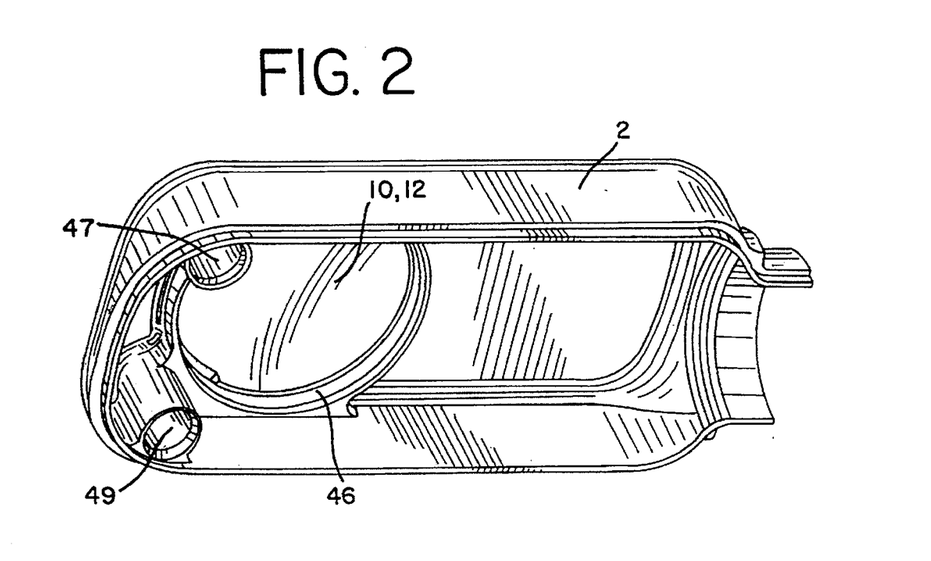
FIG. 2 is an isometric view of an upper surface of a transducer housing of the probe of FIG. 1.

As shown in FIGS. 1A and 2, the transducer housing 2 has a continuous surface 10 adjacent to the axisymmetric lens 6. In the region of the housing 2 that is adjacent to the lens 6, the continuous surface 10 of the transducer housing 2 is formed into a window 12. The window 12 mates to the shape of the lens 6. Preferably, the window 12 is integrally formed with the transducer housing 2, as shown in FIGS. 1 and 2. In the embodiment shown in FIG. 1, the radii of curvature of the window 12 match the radii of curvature of the axisymmetric lens 6.

A thin layer of a grease 14 fills an interface within the transducer housing 2 between the window 12 and the axisymmetric lens 6. The grease 14 lubricates the interface between the window 12 and the axisymmetric lens 6 and displaces air that would otherwise occupy the interface.

The transducer array 4 is mounted on a backing material 16, which is acoustically attenuative. A preferred acoustically attenuative backing material is described in U.S. Pat. No. 5,297,553 issued to Sliwa, Jr. et al., which is incorporated herein by reference. Preferably, the backing material 16 is formed from rigid polymeric or polymer-coated particles fused into a macroscopically rigid structure having remnant tortuous permeability, as shown in U.S. Pat. No. 5,297,553. This structure provides high acoustic attenuation and permits fluid passage into the backing structure during fabrication. An optional container may provide additional physical integrity to the backing material 16, and the backing material 16 may be attached to the container by an optional bonding adhesive layer. The backing materials described in U.S. Pat. No. 5,297,553 provide high acoustic attenuation. This allows a thinner backing material to be used, thereby allowing the transducer probe to be downsized.

A rotatable cable 18 projects into the transducer housing 2, as shown in FIGS. 1A–1C. Affixed to a distal end of the rotatable cable 18 is a worm 20. The worm 20 engages a worm wheel 22, as shown in FIG. 1B. The worm wheel 22 is attached via a vertical shaft 24 to a gear 26. As shown in FIG. 1C, the gear 26 engages an idler gear 28, which in turn engages a ring gear 30 attached to a turntable base 32. The turntable base 32 is attached to a pedestal 34 for a platform 36. The platform 36 supports the backing material 16, the transducer array 4, and the axisymmetric lens 6. A stationary pin 38, which is attached at one end to the transducer housing, projects into the pedestal 34.

The platform 36, the pedestal 34, and the turntable base 32 form a bobbin-like structure. A number of ball bearings 40 are contained within the pedestal 34. Preferably, the platform 36 and the pedestal 34 containing the bearings 40 is a single-piece assembly fabricated from hardened stainless steel.

A flexible circuit 42 wraps around and is anchored to the pedestal 34. The flexible circuit 42 electrically couples the transducer array 4 to a remote ultrasound control and operating system. Preferably, the flexible circuit 42 is directly coupled to the elements of the transducer array 4.

During operation of the transducer probe shown in FIGS. 1 and 2, the transducer array 4 and the axisymmetric lens 6, which is secured thereto, may be rotated by a sonographer or the ultrasound control and operating system coupled to the transducer probe. The housing 2, including the integral window 12, which is in contact with the body of the patient, typically remains stationary during rotation of the array 4 and lens 6.

Rotation of the transducer array 4 and the axisymmetric lens 6 may be brought about by turning the rotatable cable 18, which operates as a worm drive for the gears 26, 28 and 30 coupled to the turntable base 32. During rotation, the layer of grease 14 lubricates the sliding interface between the axisymmetric lens 6 and the window 12 of the housing 2 and ensures that the interface remains void free. Preferably, the turning force applied to the rotatable cable 18 is generated mechanically, such as by an electric motor. Alternatively, the turning force may be generated manually, for example by the sonographer rotating a knob. In a preferred embodiment, the turning force is applied to the rotatable cable remotely from the transducer housing 2, although a device, such as an electric motor, alternatively may be housed within the transducer housing 2 to directly drive the gear train or the turntable base 32. Although rotation of the transducer array 4 is described herein as being brought about by the rotating cable 18 and the gear train 26, 28 and 30, one of ordinary skill in the art could devise suitable alternative rotational schemes, such as using a linear actuator to slide a cable attached to a rotatably mounted transducer array.

Preferably, the entire transducer housing 2 is formed from an acoustically transmissive material, such as a thermoplastic material. The preferred thermoplastic material is TPX™ from Mitsui Petrochemicals (America) Ltd., 250 Park Ave., Suite 950, New York, N.Y. 10177. Because the entire transducer housing 2 is formed from an acoustically transmissive material, the acoustic window 12 may be integrally formed in the transducer housing 2 by reducing the thickness of the housing 2 in the area above the transducer array 4 and lens 6. It should be noted that formation of the window 12 does not require any opening in the transducer housing 2. The window 12 and the transducer housing 2 form a continuous surface 10 adjacent to the lens 6. Accordingly, additional process steps are not required to seal the window 12 against the ingress of bodily fluids, sterilant solutions, and cleaning solutions.

The thickness of the window 12 portion of the transducer housing 2 may be constant and equal to one-half wavelength of the transmitted acoustic energy at the center frequency of the transducer array 4 in the housing material. For example, if the center frequency of the transducer array 4 is 5 MHz, the window 12 should be 0.2 mm thick, where the acoustic velocity in the thermoplastic material is assumed to be 2000 ms$^{-1}$.

Alternatively, the thickness of the window 12 portion of the continuous surface 10 of the transducer housing 2 may vary as a function of distance from the axis 8. For example, the window 12 may be formed into an axisymmetric converging lens by increasing the thickness of the window 12 as a function of increasing distance from the axis 8 (assuming that the velocity of sound in the housing material is greater than the velocity of sound in the body). Similarly, the window 12 may be formed into an axisymmetric diverging lens by decreasing the thickness of the window 12 as a function of increasing distance from the axis 8. Thus, to form the window 12 portion of the continuous surface 10 into a lens, the outer surface 11 of the window 12 will have a different curvature than the inner surface 13 of the window 12. With this alternative embodiment, the probe may be constructed with or without the lens 6. If the lens 6 is present, then the surface 13 of the window 12 that is adjacent to the lens 6 is formed to mate with the lens 6, and the focal length, F, of the assembly is:

$$\frac{1}{F} = \frac{1}{F_{lens}} + \frac{1}{F_{window}} \quad (1)$$

In addition, the thickness of the window 12 portion of the continuous surface 10 may be varied to obviate reverberation artifacts that may otherwise occur if the window 12 is a constant thickness.

The thermoplastic Mitsui TPX™ material is preferred for the housing 2 because of its high modulus and low density, which provide structural rigidity and relative acoustic transparency. In addition, the high dielectric strength of the TPX™ material allows the thickness of the lens 6 to be reduced, further reducing the profile of the transducer housing 2.

The lens 6 is formed from silicone rubber, preferably Dow Corning Q5-8008 having approximately forty-two percent silicon dioxide filler. Alternatively, Dow Sylgard 577 Primerless Silicone Adhesive RTV-560 may be used, although with a slight degradation in performance.

The grease 14 provides lubrication between the stationary housing window 12 and the rotating lens 6 attached to the transducer array 4. In addition, the grease 14 displaces air that may otherwise be present between the window 12 and the lens 6. The viscosity of the grease 14 should be chosen to minimize air voids and channeling, which may otherwise occur as a result of rotating the array 4 and lens 6.

Furthermore, the grease 14 should be chemically compatible with the lens 6 material and housing 2 material. Preferably, the grease 14 is made from synthetic base oils and has a low base-oil kinetic viscosity in the range of 10-40 centistokes measured at 40° C. Acceptable greases include fluorosilicone, polyalphaolefin, and fluoroether greases.

As shown in FIG. 1, the axisymmetric lens 6 may have a cylindrical side wall 44, which descends beyond the face of the transducer array 4. A recess 46, shown in FIG. 2, may be formed in the continuous surface 10 of the transducer housing 2 to mate with the shape of the lens 6. A grease seal 48 is positioned around the cylindrical wall 44 of the lens 6, as shown in FIG. 1, to contain the grease 14 to the volume between the lens 6 and the window 12. Alternatively, a seal may be integrally formed on the cylindrical wall 44 of the lens 6.

Filling ports, such as filling ports 47 and 49 as shown in FIG. 2, may be added to the transducer housing 2 to facilitate assembly, minimize air voids, and allow for addition of grease. The filling ports 47 and 49 are substantially cylindrical bores through the transducer housing 2 that are connected by a pathway to the grease-filled interface between the window 12 and the axisymmetric lens 6. A grease plug may be used to seal the filling port. The filling ports 47 and 49 facilitate assembly by providing access to the interface for either adding grease or allowing excess grease to be expelled. Due to the small volume of grease in the interface, thermally induced pressure changes could result in a loss of grease 14 through the seal 48 absent the filling ports. Air voids are minimized by providing pressure relief, under conditions of thermal expansion and contraction, to the grease-filled interface via the grease plugs, which are allowed to slide in the filling ports 47 and 49 in response to expansion or contraction of the grease.

The ultrasonic scanhead shown in FIG. 1 may be assembled by casting the lens 6 with the side wall 44 to the transducer array 4. The seal 48 is then positioned around the side wall 44 and grease 14 is applied to the lens 6 and/or the window 12. The array 4, with the previously attached lens 6, is then mated to the housing 2 by inserting the lens portion into the recess 46 and squeezing out any excess grease 14, or air voids within the grease 14, through the filling ports 47 and 49. Alternatively, the lens 6 and array 4 subassembly may be inserted into the recess 46, with the grease 14 being added after assembly through one of the filling ports 47 and 49. Excess grease 14 may exit the housing once the interface is filled through another filling port.

In another embodiment, the axisymmetric lens 6 may be secured to the recess 46 in the housing 2, in which case the lens 6 would remain stationary with the housing 2 and the transducer array 4 would rotate below the lens 6. Alternatively, the recess 46 may be removed from the transducer housing 2 and the axisymmetric lens 6 secured about its periphery to the transducer housing 2, in place of the recess 46, forming a stationary seal. In this alternative, the transducer array 4 would likewise rotate below the stationary lens 6.

In an alternative embodiment of the present invention, the grease 14, which fills the interface between the lens 6 and the window 12, is replaced by a gel. The gel is a soft, jellylike semi-solid that adheres to both the lens 6 and the window 12, but is sufficiently flexible to allow the lens 6 to rotate to some extent below the window 12.

For a transducer array that scans within a two-dimensional plane, it is desirable that the array be capable of rotating through approximately 180 degrees. Therefore, the gel should be capable of withstanding at least a ±90 degree rotation of the lens 6 with respect to the window 12. If the gel is to withstand a ±90 degree rotation of the lens 6 without tearing, it must be able to elongate and shear without tearing. The total shear and elongation required for any particular ultrasound probe design is a function of the lens diameter and the thickness of the gel. For example, in a preferred embodiment in which the lens 6 has a diameter of approximately 0.5 inches and the gel thickness is approximately 0.010 inches throughout the interface, the total shear and elongation required of the gel is approximately 4000%. This total will vary for probes having a different lens diameter and/or a different gel thickness and may be optimized during probe design by varying the required gel thickness and/or lens diameter.

The gel is preferably a two-part, silicone based, curable material. A first part of the material is a fluid and a second part of the material is a fluid with an additive. When the first part and the second part are combined and cross-linked by curing, the two-part material becomes a gel in which the fluids are substantially immobilized. After curing, the gel has a two-dimensional semi-solid structure that has some elastomeric properties.

In its preferred form, the gel is transparent to the remote ultrasound control and operating system, i.e., it has no effect on the focusing of the transmitted and received ultrasound signals. Accordingly, the gel should have a uniform thickness across the interface between the lens 6 and the window 12, and the acoustic impedance of the gel should be matched to the body being inspected. For medical applications, the velocity of sound in the gel is preferably 1540 meters per second, and the density of the gel is preferably 1. By matching the velocity of sound in the gel and the density of the gel to the body, small variations in the gel thickness that may occur during use of the probe will not result in an undesirable focusing effect. A suitable, commercially available gel for this application is OC-447, which is available from Nye Lubricants, of New Bedford, Mass. In an alternative embodiment, the the thickness of the gel, the velocity of sound in the gel, or both, may be varied in accordance with known acoustic principles to produce focusing or defocusing of the acoustic energy in the gel. Therefore, the gel may entirely replace both the lens 6 and the grease 14. In this case, the velocity of sound in the gel is preferably less than 1540 meters per second.

When assembling the ultrasonic scanhead shown in FIG. 1, the two parts of the gel are first mixed and vacuum degassed. The two-part liquid mixture is then placed into the interface between the lens 6 and the window 12, and degassed again, if necessary. The lens 6, which has previously been cast to the transducer array 4, is then positioned against the mixture and the window 12 so that the transducer array 4 is oriented at approximately 90 degrees with respect to its travel limits, i.e., the midpoint of its approximately 180 degree rotation. This assembly is then heat cured to produce a gel from the mixture, with the gel adhering to both the lens 6 and the window 12. By setting the array 4 orientation to the midpoint of its travel limits, the required elongation of the gel, and the shearing and tearing effects of rotating the array 4, are minimized. A temporary seal, such as the seal 48 in FIG. 1, may be used to prevent the mixture from flowing out of the interface between the lens 6 and the window 12 while it is curing.

Alternatively, the two-part mixture may be cured onto either the lens 6 or the window 12. After the mixture is cured to gel form, the transducer array 4, with the previously attached lens 6, may be mated to the housing 2 by inserting the lens portion into the recess 46 below the window 12, as described above.

In comparison to using a grease 14 lubricant, the gel provides the advantage of not requiring a seal, such as the grease seal 48, to keep it in place. In effect, the gel is self-sealing. In addition, the filling ports 47 and 49 and the grease plugs become unnecessary. When a seal is used, tight tolerances should be maintained on the seal itself, all mating components, and on the alignment of the array 4, lens 6 and window 12 along the axis of rotation 8 to prevent breakage or temporary breach of the seal. Since the gel does not require a seal to keep it in place, these tolerances may be relaxed making the components of the probe easier to assemble. In addition, the total number of parts in the probe is reduced and the risk of grease leaking out of the interface is eliminated. Furthermore, by removing a seal from the probe, the gel embodiment may allow the width of the probe to be reduced.

The ultrasonic transducer array 4 may be excited to produce a two-dimensional image of one slice through a three-dimensional target. The plane containing the slice is referred to herein as an object plane. Focusing in one direction, herein referred to as the elevation direction, is provided by the axisymmetric lens 6. For the array and lens geometry shown in FIGS. 1 through 4, the elevation direction is the direction parallel to the long axis of the elements of the transducer array 4. Focusing in the perpendicular direction, herein referred to as the azimuthal direction, may be achieved electronically using known delay and sum techniques, such as the techniques described in U.S. Pat. Nos. 4,140,022 and 4,550,607 issued to Maslak. The azimuthal direction is perpendicular to the long axis of the elements of the transducer array 4. Azimuthal focusing provides focusing of acoustic energy at focal points within the object plane.

Because the thickness of the axisymmetric lens 6 may vary along the azimuthal direction, thereby causing some azimuthal focusing, the delay and sum technique for electronically focusing in the azimuthal direction should be modified to compensate for a lens-induced component of azimuthal focusing. The precise geometry and focusing characteristics of the axisymmetric lens are first determined. The ultrasound control and operating system can then inject compensating electronic delays by the transmitting and receiving electronics in order to account for the lens-induced component of azimuthal focusing.

Timing effects introduced by an azimuthally curved lens may be accounted for by applying Fermat's Shortest Path Law and geometric ray tracing techniques to the lens geometry and adjusting corresponding electronic delays. For a given axisymmetric lens geometry, the minimum time path from each element of the transducer array 4 through the axisymmetric lens 6 to each focal point within the object plane may be computed. For a lens in which the velocity of sound in the lens is less than the velocity of sound in the body, such as a silicone rubber lens, the minimum time path is longer for an array with a lens than it would be if there were no lens. Delay times must, therefore, be modified in both the transmit and receive circuitry to compensate for this increase in propagation time. Alternatively, the required compensating delays may be derived by applying Snell's Law and geometric ray tracing techniques to the lens geometry.

Figures 3, 4:
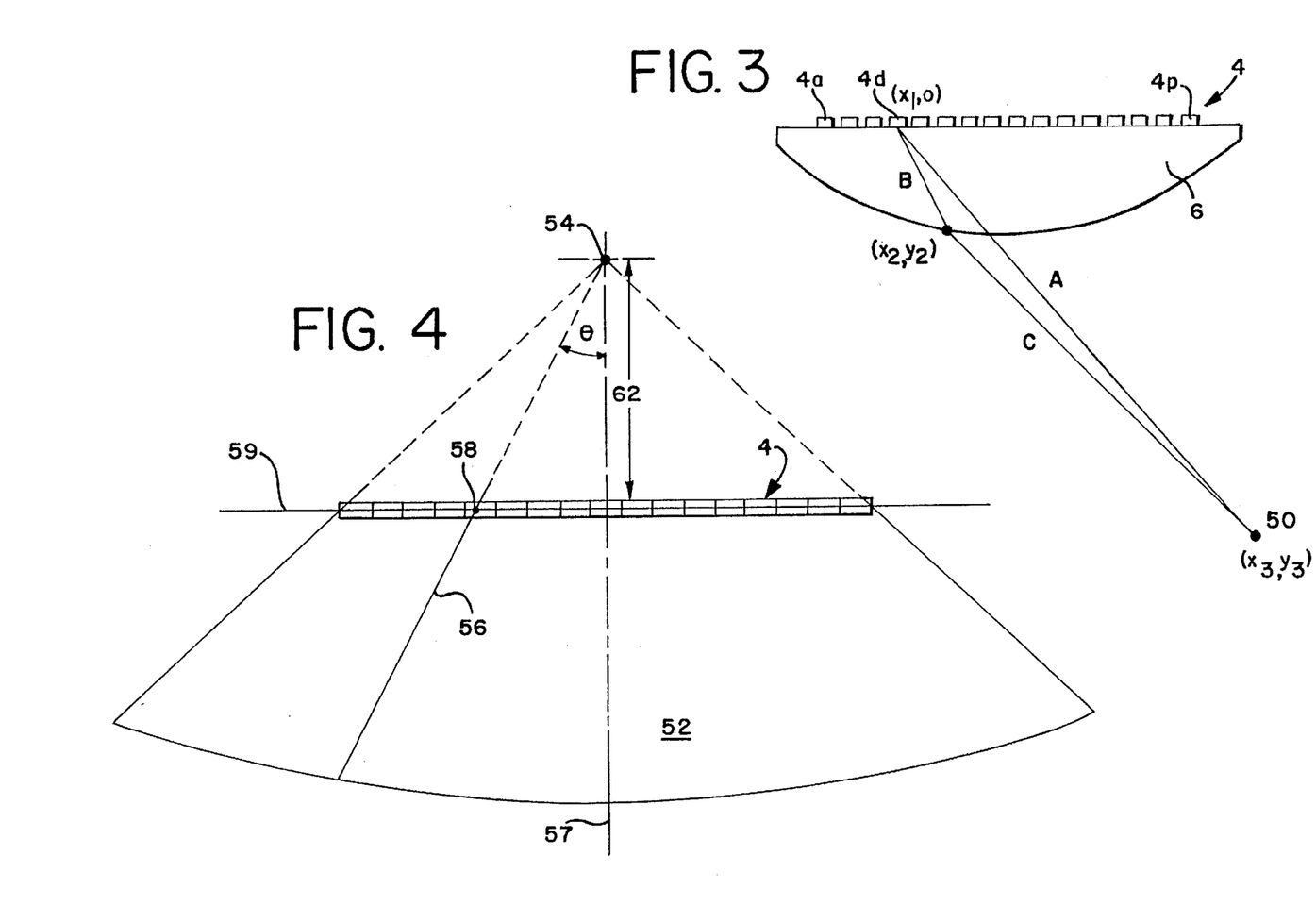
FIG. 3 is a sectional view along the azimuthal axis of an ultrasonic transducer array and a lens as shown in the probe of FIG. 1.
FIG. 4 illustrates an image plane formed by scanning a transducer array in a variable vertex format.

Referring now to FIG. 3, a section of the transducer array 4 and the axisymmetric lens 6 assembly is shown, the section being taken along the azimuthal direction through the center of the array. Individual transducer elements $4a$ . . . $4p$ are shown adjacent to the axisymmetric lens 6. A focal point 50 within the body is illustrated.

For a given axisymmetric lens geometry, the minimum time path from each element of the transducer array 4 through the axisymmetric lens 6 to each focal point 50 within the object plane is calculated as follows. Given a transducer element 4$d$ centered at the point $(x_1, 0)$ and a desired focal point 50 at $(x_3, y_3)$, the minimum time path for the transducer elemented 4$d$ will cross the interface between the lens 6 and the body at some point $(x_2, y_2)$. The minimum propagation time, t, is:

$$t = \frac{B}{C_{lens}} + \frac{C}{C_{body}} \tag{2}$$

In equation 2, B is the path length within the lens and C is the path length within the body corresponding to the minimum time path. $C_{lens}$ and $C_{body}$ are the velocities of sound in the lens and body, respectively.

If the axisymmetric lens 6 is a spherical lens, then the thickness, T, of the lens at the point $(x_2, y_2)$ is:

$$T(x_2) = y_2 = T - R + \sqrt{R^2 - x_2^2} \tag{3}$$

In equation 3, T is the maximum thickness of the spherical lens, which is located over the center element of the array 4, and R is the radius of curvature of the lens. The equation for T(x) for aspherical lens may be approximated by the equation for T(x) for a parabolic lens:

$$T(x_2) = y_2 = T - \frac{x_2^2}{2R} \tag{4}$$

Substituting for $y_2$, equation (2) for the minimum propagation time, t, can be rewritten as a function of the variable $x_2$:

$$t = \frac{1}{C_{lens}} \sqrt{(x_2 - x_1)^2 + T^2(x_2)} + \tag{5}$$

$$\frac{1}{C_{body}} \sqrt{(x_3 - x_2)^2 + [y_3 - T(x_2)]^2}$$

The coordinate $x_2$ that minimizes t can then be found, for example by an iterative search. Once $x_2$ is found for transducer element 4$d$, which is centered at $x_1$, the difference $(x_2-x_1)$ can be used as an initial value in the search for $x_2$ for neighboring transducer elements, 4$c$ and 4$e$.

Knowing the value of $x_2$ corresponding to the minimum propagation time t for each element 4$a$ ... 4$p$ of the array 4, the corresponding increase in propagation time due to the lens 6 for each element of the array 4 is:

$$\Delta t = \frac{1}{C_{lens}} B + \frac{1}{C_{body}} [C - A] \tag{6}$$

$$= \frac{1}{C_{lens}} \sqrt{(x_2 - x_1)^2 + T^2(x_2)} +$$

$$\frac{1}{C_{body}} [\sqrt{(x_3 - x_2)^2 + [y_3 - T(x_2)]^2} -$$

$$\sqrt{(x_3 - x_1)^2 + y_3^2} \,],$$

where A is the distance between the transducer element and the focal point 50 at $(x_3, y_3)$. The delay for each element of the array is determined by inputting the appropriate value of $x_2$. Corresponding delays must be calculated for each focal point within the object plane. Because the minimum time path is greater for an array with a lens than it is without a lens, the change in delay time, $\Delta t$, is subtracted from the delay time that the ultrasound control and operating system would apply in the absence of the axisymmetric lens to achieve azimuthal focusing. Determination of the delay time that the ultrasound control and operating system would apply in the absence of a lens is described in U.S. Pat. Nos. 4,140,022 and 4,550,607.

The transducer probe described herein may be used with an ultrasound operating and control system for scanning in a variety of scan and display formats, including, but not limited to, a variable vertex format as described in U.S. Pat. Nos. 5,148,810, 5,261,408, and 5,235,986 issued to Maslak et al., which are incorporated herein by reference. The variable vertex scan and display format provides an expanded field of view for a given transducer array geometry by transmitting ultrasonic pressure waves and receiving return echoes on a set of spatially non-overlapping acoustic scan lines, wherein each acoustic scan line originates at an arbitrary point on and at an arbitrary angle to the face of the array. The set of acoustic scan lines is formed by software control. As described in U.S. Pat. No. 5,148,810, the set of acoustic scan lines may align with rays emanating from a common vertex located a selectable distance behind the face of the transducer array. The distance between the vertex and the face of the transducer array 4 is referred to herein as the vertex offset 62.

Referring now to FIG. 4, the transducer array 4 is shown. A set of acoustic scan lines produces a field of view 52 in the variable vertex format. The set of acoustic scan lines appears to emanate from a common vertex 54. An acoustic scan line 56 from the set of acoustic scan lines is illustrated. The acoustic scan line 56 originates at a point 58 on the face of the transducer array 4 and emanates at an angle $\theta$ with respect to the normal 57 to the face of the transducer array 4. The vertex offset 62 is illustrated.

The point 58 on the face of the transducer array 4 at which the acoustic scan line 56 originates is referred to herein as the acoustic line origin. For a given transducer array geometry, the acoustic line origin is selectable under software control. The acoustic line origin for the planar array of FIG. 4 occurs on a line 59 connecting the individual transducer elements at the point corresponding approximately to the center of mass of the apodization function applied to the array 4. Thus, controlling the acoustic line origin is achieved by assigning apodization values to each element of the transducer array 4 so that the center of mass of the apodization function corresponds to the desired point 58 on the face of the transducer array 4, as described in U.S. Pat. No. 5,148,810.

In order to operate the transducer probe of FIG. 1 in the variable vertex scan and display format, the ultrasound control and operating system compensates for the presence of the axisymmetric lens 6 between the transducer array 4 and the body to be imaged. The axisymmetric lens 6 a) increases the distance between the vertex and the body to be imaged, and b) refracts the acoustic scan lines.

Figure 5A:
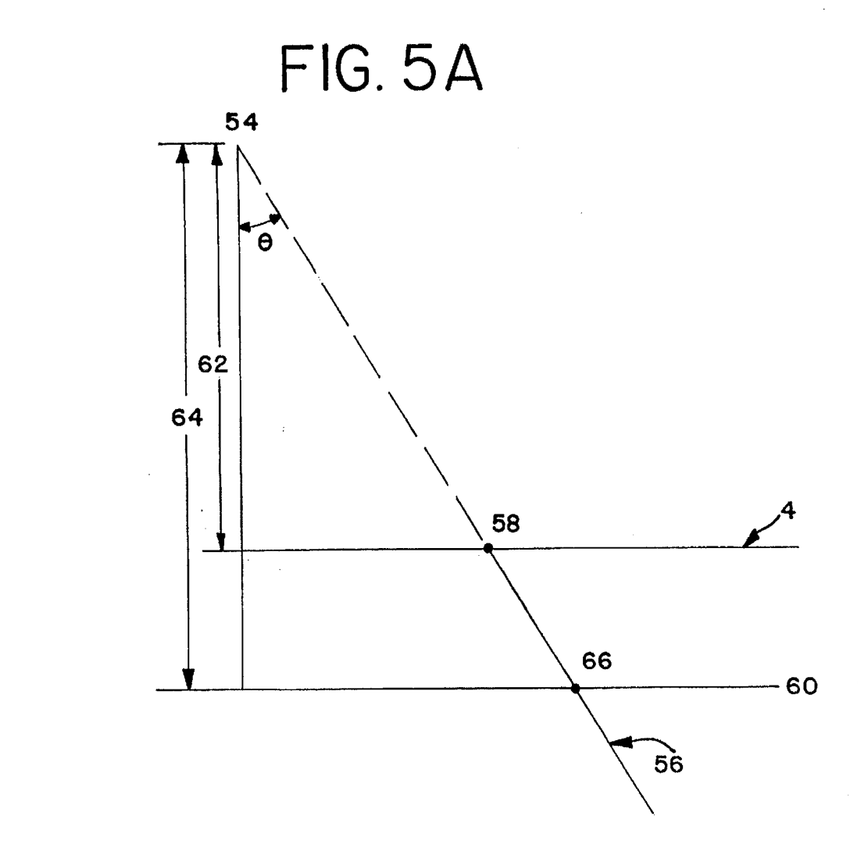
FIGS. 5A and 5B illustrate an acoustic scan line emanating from a vertex and propagating through a constant sound velocity medium and an axisymmetric lens, respectively.

FIG. 5A illustrates the increased distance between the vertex 54 and the body to be imaged 60 due to the presence of the lens 6. When scanning without the lens 6, the vertex offset 62 is the distance between the vertex 54 and the face of the transducer array 4. The ultrasound control and operating system assumes, when the lens 6 is present, that the body begins at a plane 60, which is parallel to the face of the transducer array 4. The acoustic scan line 56 originates at the point 58 on the face of the transducer array 4 and at the angle $\theta$ with respect to the normal to the face of the array. The acoustic scan line 56 passes through the plane 60 at a point 66.

The ultrasound control and operating system compensates for the increase in distance between the vertex 54 and the body to be imaged by using an adjusted vertex offset 64 that accounts for the thickness of the lens 6. The vertex offset 64, which accounts for the lens 6, $VA_{lens}$ is:

$$VA_{lens} = VA + \frac{C_{body}}{C_{lens}} T \qquad (7)$$

where VA is the vertex offset for a constant sound velocity (i.e. lens-less) medium, $C_{body}$ is the sound velocity in the body, $C_{lens}$, is the sound velocity in the lens 6, and T is the maximum thickness of the lens.

Figure 5B:
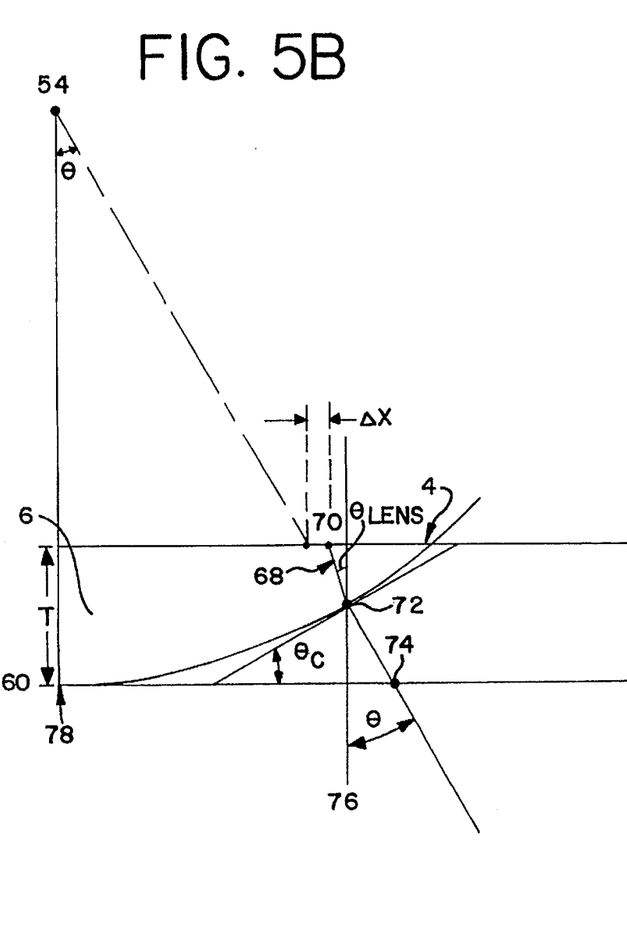

The presence of the lens 6 in front of the array 4 will cause the acoustic scan line to refract, thereby requiring a shift in the acoustic line origin by some distance, $\Delta x$, in the azimuthal direction. FIG. 5B is a sectional view of the transducer array and the axisymmetric lens 6, the section being taken along the azimuthal direction through the array 4. An acoustic scan line 68 originates at a point 70 on the face of the transducer array 4. The acoustic scan line 68 propagates through the lens 6 to the lens/body interface at a point 72. The acoustic scan line 68 then passes through the plane 60, where imaging begins to take place, at a point The acoustic scan line 68 propagates through the lens 6 at an angle $\theta_{lens}$ with respect to a normal 76 to the face of the transducer array 4 and propagates through the body at an angle $\theta$ with respect to the normal 76. The angle of the lens/body interface at the point 72 with respect to the plane 60 is designated $\theta_c$.

The appropriate shift, $\Delta x$, in the acoustic line origin 70 must be computed for the acoustic scan line 68 so that the point 74, shown in FIG. 5B, coincides with the point 66, shown in FIG. 5A. The shift in acoustic line origin, $\Delta x$, must be computed for each acoustic scan line in the set of acoustic scan lines. The shift in the acoustic line origin, $\Delta x$, induced by the lens 6 may be determined as follows.

If x refers to the horizontal position of a point as measured from the center 78 of the transducer array 4, and y refers to the point's vertical position as measured from the plane 60 where imaging begins, then the horizontal position of the point 74 where the acoustic scan line 68 crosses the imaging plane 60 is:

$$x_{74} = x_{66} = VA_{lens} \cdot \tan\theta \qquad (8)$$

For a spherical axisymmetric lens 6, the horizontal position of the point 72 where the acoustic scan line 68 crosses the lens/body interface is:

$$x_{72} = x_{74} - y_{72} \cdot \tan\theta, \qquad (9)$$

$$= VA_{lens} - \frac{x_{72}^2}{2R} \cdot \tan\theta \text{ (parabolic approximation)}, \qquad (10)$$

$$= \frac{R}{\tan\theta} \left[ -1 + \sqrt{1 + \frac{2VA_{lens}\tan^2\theta}{R}} \right] \qquad (11)$$

where R is the radius of curvature of the lens 6 in the azimuthal direction. Equation (11) is arrived at by solving the quadratic equation (10) and taking the appropriate root. Equation (11) can be simplified using the approximation:

$$\sqrt{1+x} = 1 + \frac{1}{2} x - \frac{1}{8} x^2 + \frac{1}{16} x^3 - \frac{5}{128} x^4 \text{ if } |x| \ll 1. \qquad (12)$$

With this approximation, the horizontal position of the point 72 is:

$$x_{72} = VA_{lens}\tan\theta - \frac{VA_{lens}^2}{2R} \tan^3\theta + \frac{VA_{lens}^3}{2R^2} \tan^5\theta - \frac{5VA_{lens}^4}{8R^3} \tan^7\theta. \qquad (13)$$

The angle $\theta_c$ of the lens/body interface with respect to the imaging plane 60 at the point 72 is:

$$\theta_c = a\tan\left[ \frac{x_{72}}{\sqrt{R^2 - x_{72}^2}} \right], \qquad (14)$$

$$= a\tan\left[ \frac{x_{72}}{R} \right] \text{ (parabolic approximation)} \qquad (15)$$

$$= \frac{x_{72}}{R} \text{ (small angle approximation)}. \qquad (16)$$

The angle $\theta_{lens}$ of the acoustic scan line 68 within the lens 6 with respect to the normal 76 is given by Snell's Law as:

$$\theta_{lens} = a\sin\left[ \frac{C_{lens}}{C_{body}} \sin(\theta - \theta_c) \right] + \theta_c \qquad (17)$$

Using the angle $\theta_{lens}$ the horizontal position of the acoustic line origin 70 is:

$$x_{70} = x_{72} - \left( T - R + \sqrt{R^2 - x_{72}^2} \right) \tan\theta_{lens} \qquad (18)$$

and the acoustic line origin shift, $\Delta x$, is:

$$\Delta x = x_{70} - VA + \tan\theta \qquad (19)$$

The acoustic line origin shift, $\Delta x$, provides the desired point on the face of the transducer array to be equated with the center of mass of the apodization function for the transducer array.

The start-of-line delay should also be adjusted on an acoustic line-by-line basis to reduce image distortion. The start-of-line delay due to the lens 6 is the time it takes to propagate from the face of the transducer array, through the lens 6, to a plane where the ultrasound control and operating system assumes the body begins, i.e. the imaging plane 60, and back again. The ultrasound control and operating system typically assumes that the body begins at the plane that is parallel to the face of the transducer array 4 and is tangential to the lens 6.

Using the values for the acoustic line origin, the line-by-line variation in the start-of-line delay may be approximated as follows:

$$\Delta SOL = 2 \left[ \frac{1}{C_{lens}} \cdot \frac{1}{\cos\theta_{lens}} (T - R + \sqrt{R^2 - x^2}) + \frac{1}{C_{body}} \cdot \frac{1}{\cos\theta} (R - \sqrt{R^2 - x^2}) \right] \qquad (20)$$

Ultrasound data acquired after the start-of-line delay are displayed by the ultrasound control and operating system, while earlier received data are discarded.

It is intended that the foregoing detailed description be regarded as illustrative rather than limiting and that it is understood that the following claims, including all equivalents, are intended to define the scope of the invention.

We claim:

1. An ultrasonic transducer probe, comprising:
   an ultrasound transducer array disposed within a housing of the probe; and
   a resilient material filling an interface between the ultrasound transducer array and the housing, the resilient material being formed from a curable gel and being self-sealing against leakage with respect to the housing.

2. An ultrasonic transducer probe as claimed in claim 1, wherein the resilient material adheres to an acoustic lens and the housing, the acoustic lens being positioned between the array and the housing.

3. An ultrasonic transducer probe as claimed in claim 2, wherein the resilient material forms a self-sealing interface between the lens and the housing.

4. An ultrasonic transducer probe as claimed in claim 1, wherein the resilient material comprises silicone.

5. An ultrasonic transducer probe as claimed in claim 1, wherein the housing comprises an acoustic window, the window being aligned along an axis of rotation with the array and the lens.

6. Art ultrasonic transducer probe as claimed in claim 5, wherein the resilient material is positioned between the lens and the window.

7. An ultrasonic transducer probe as claimed in claim 6, wherein the resilient material adheres to the lens and the window.

8. An acoustic transducer probe as claimed in claim 1, wherein the velocity of sound in the resilient material is approximately 1540 meters per second.

9. An acoustic transducer probe as claimed in claim 1, wherein the resilient material comprises a two-part curable gel.

10. An ultrasonic transducer probe, comprising:

an ultrasound transducer array disposed within a housing of the probe, wherein the array transmits and receives ultrasound waves;

means for rotating the array; and a resilient material filling an interface between the ultrasound transducer array and the housing, the resilient material being of such a type so as to withstand rotation of a first surface with respect to the housing throughout the range of rotation of the array without tearing and being self-sealing against leakage with respect to the housing.

11. Art ultrasound transducer probe as claimed in claim 10, wherein the resilient material focusses the ultrasound waves.

12. An ultrasound transducer probe as claimed in claim 11, wherein the velocity of sound in the resilient material is less than 1450 meters per second.

13. An ultrasound transducer probe as claimed in claim 10, wherein the resilient material adheres to an acoustic lens and the housing, the acoustic lens being positioned between the array and the housing.

14. An ultrasonic transducer probe as claimed in claim 13, wherein the housing comprises an acoustic window, the window being aligned along an axis of rotation with the array and the lens.

15. An ultrasonic transducer probe as claimed in claim 14, wherein the resilient material is positioned between the lens and the window.

16. An ultrasonic transducer probe as claimed in claim 15, wherein the resilient material adheres to the lens and the window.

17. An ultrasonic transducer probe as claimed in claim 10, wherein the resilient material comprises silicone.

18. An ultrasonic transducer probe as claimed in claim 10, wherein the resilient material comprises a two-part gel.

* * * * *